(12) United States Patent
MacLeod

(10) Patent No.: US 6,589,211 B1
(45) Date of Patent: Jul. 8, 2003

(54) MODIFIED TROCAR AND METHODS OF USE

(76) Inventor: Cathel MacLeod, 46 Sunnyfield La., Cumberland Center, ME (US) 04021

(*) Notice: Subject to any disclaimer, the term of this patent is extended or adjusted under 35 U.S.C. 154(b) by 0 days.

(21) Appl. No.: 09/390,053

(22) Filed: Sep. 3, 1999

Related U.S. Application Data

(63) Continuation-in-part of application No. 08/949,173, filed on Oct. 10, 1997, now Pat. No. 5,947,922, which is a division of application No. 08/756,761, filed on Nov. 26, 1996, now Pat. No. 5,741,298, which is a continuation-in-part of application No. 08/431,126, filed on Apr. 28, 1995, now abandoned.

(51) Int. Cl.⁷ ............................................. A61M 5/00
(52) U.S. Cl. ................................. 604/164; 604/164.01
(58) Field of Search ................. 604/164.01, 164.04, 604/164.09, 166.01, 256, 264; 600/198, 185

(56) References Cited

U.S. PATENT DOCUMENTS

| | | | | |
|---|---|---|---|---|
| 5,411,519 A | * | 5/1995 | Tovey et al. | 606/207 |
| 6,099,505 A | * | 8/2000 | Ryan et al. | 604/167.04 |

* cited by examiner

*Primary Examiner*—Manuel Mendez
(74) *Attorney, Agent, or Firm*—Pierce Atwood

(57) ABSTRACT

A modified trocar system to assist in surgical procedures. In one embodiment, the system is designed to assist in lifting lift a body wall in order to perform surgical procedures within the body cavity without establishing insufflation. The flanged trocar embodiment includes an extended flange forming a portion of the trocar body wall that may be inserted through the incision and deployed against either the interior surface of the body wall, or the interior surface of a protective sealing ring. A lifting mechanism forming a portion of the upper part of the flanged trocar is used in conjunction with the extended flange to enable the surgeon to draw the retained trocar upward in order to provide additional access to the body cavity under the tented body wall. In a more general embodiment of the invention, the modified trocar is directed through an existing incision and is used in an inward-to-outward manner to create a second smaller incision. The second smaller incision is designed to enable the deployment of some operating equipment or attachment device. Larger equipment may then be deployed through the larger first incision and coupled to the unit inserted into the smaller incision. In this way, a variety of manipulations may take place within the body cavity with minimal incision sizes and reduced traffic into and out of the incisions.

10 Claims, 9 Drawing Sheets

MODIFIED TROCAR AND METHODS OF USE

CROSS REFERENCE TO RELATED APPLICATIONS

This application is a continuation-in-part of U.S. application Ser. No. 08/949,173, filed Oct. 10, 1997, entitled "Modified Surgical Gloves and Methods of Use," now U.S. Pat. No. 5,947,922 which is a divisional application of U.S. application Ser. No. 08/756,761, filed Nov. 26, 1996, entitled "Method and Devices for Video-Assisted Surgical Techniques, now U.S. Pat. No. 5,741,298, issued Apr. 21, 1998, which is a continuation-in-part of U.S. application Ser. No. 08/431,126, filed Apr. 28, 1995, now abandoned. Applicant claims the priority benefit of the referenced applications that describe inventions conceived of by Applicant.

BACKGROUND OF THE INVENTION

1. Field of the Invention

This invention relates to a surgical operating system and one or more devices for performing such surgery. More particularly, the present invention relates to a device that permits effective lifting of the body wall without the need to provide insufflation. The present invention may be used in association with the surgical devices and related procedures described and claimed in the cross-referenced applications.

2. Description of the Prior Art

For many years most surgery was performed using an open technique. The surgeon made an incision dictated by the need to directly observe the area of interest and to insert his or her hand or hands, and/or one or more instruments to perform manipulations within the body cavity accessed through the incision. Retractors and assistants help to provide means of access. For many procedures these incisions are as long as 20 centimeters, traumatic, and painful. This translates into a painful recovery, prolonged hospitalization with a slow return to a normal functional state, and significant cost.

An alternative to open surgery, endoscopic surgery, has also been available for many years, though not as widely applied. Through an endoscope—a tubular optical system for viewing the interior of an organ or body cavity—tissues can be observed. An endoscope is used by making a small incision in the appropriate body covering. A hollow tube, or port, usually 10–25 cm in length and 5–30 mm in diameter, is placed through the incision and the endoscope is placed through the hollow tube. Through various other incisions and ports, other instruments can be placed into a body space for manipulation, grasping, cutting, coagulation etc., similar to open surgery. In the abdomen and pelvis the optical tube is called a laparoscope and the method laparoscopic surgery.

This laparoscopic surgical method usually includes a step of expanding the body cavity with air, inducing a state of pneumoperitoneum, which enhances the surgeon's view and ability to make manipulations. This is accomplished by one of two techniques, air insufflation or abdominal wall lifting. Abdominal wall lifting creates negative pressure within the cavity in relation to the atmosphere, drawing in air through a small incision when the wall is lifted. The disadvantage with this technique is that observation is imperfect. A tent is created with a central peak and a collapsed perimeter. Though most-structures have midline attachments, most endoscopic manipulations take place in the periphery. This is where visualization with this technique is worst. Insufflation is a positive pressure system using a medicinal vapor such as carbon dioxide or nitrogen injected into the peritoneal cavity to balloon the abdominal wall. Expansion is more uniform. Vision is better. This is the most widely used technique. Because of the positive pressure, however, the abdomen must be sealed to maintain expansion. This requires that all incisions and ports be sealed. Insufflation also has adverse respiratory and hemodynamic consequences due to positive pressure inhibiting chest expansion and venous blood return to the heart.

Though endoscopic surgery has been available for many years, its application has increased due primarily to the development of video monitoring equipment. This has allowed all members of the surgical team to observe, though indirectly, what only the surgeon could previously observe through a laparoscope. In some cases visualization is better than with direct observation. This has led to renewed interest and investigation of these techniques.

The benefit of endoscopic surgery is the limited incisional trauma, improved cosmesis, and decreased pain. For several simple techniques, such as laparoscopic cholecystectomy, this has translated into decreased hospitalization and earlier return to normal function, though cost savings is debated.

While some open surgical procedures have been adapted to laparoscopic technique, there are limitations with this method, particularly with more complex procedures. Fundamental problems relate to the access tubes used for inserting the various manipulative instruments. While limiting incisional trauma, the small diameter of these tubes dictates and limits the design of the inserted instruments. To achieve similar function as in open surgery, equipment becomes complex and therefore more expensive. There is also added risk with each access tube. Each tube requires a stab-wound of the body wall, risking injury to contained viscera with each puncture.

Equally important has been the impact on the surgeon's ability to manipulate tissue. The visual field may have been improved. However, tactile sensation, depth perception, and proprioceptive awareness of tissues have been markedly reduced by instruments that insulate the surgeon from the operative field. As the surgeon continually confirms that that which is done is that which is desired, procedural and anesthesia time increase. Furthermore, the limited access enabled by each port dictates that multiple ports be used. As procedural complexity increases, the surgeon must adapt to a continuously changing and less predictable environment than with simple procedures. The number of ports, and the risk and incidence of complications increases. The requirement for highly skilled and coordinated surgical teams also increases. This has resulted in long learning curves and has limited wide application of these procedures for complex cases.

One device in common usage to establish relatively small incisions for the insertion of equipment therethrough is the trocar. The trocar has a sharp end designed to pierce the skin as the surgeon presses it down to pierce through the skin. It may also pierce the underlying viscera unless great care is taken, particularly in view of the flexibility of the body wall. The trocar includes a cannula or tube used for drainage or for the insertion of a device into the body cavity. Since it is desirable to minimize the patient's wounds, there is an effort made to minimize the size of an incision associated with trocar use. As a result, the size of the tube used in the trocar-created incision is generally relatively small. It therefore can only be used to pass relatively small devices into the body cavity. Moreover, the narrow tube severely restricts maneuverability of the device contained therein. Therefore, though trocars offer the advantage of wound minimization, they are of some danger to the viscera, they are of restricted dimensions for allowing the passage of devices of interest therethrough, and they permit limited tactile manipulation.

One device apparently designed to assist in endoscopic procedures is described in U.S. Pat. No. 5,366,478 issued to Brinkerhoff. Brinkerhoff teaches a toroidal unit that is designed to be inflated so as to create an apparent sealing component through the center of which an arm or instrument is supposed to pass. However, Brinkerhoff specifically states that the "approximate height of the first (exterior) toroidal section 11 should be at least 2 inches to safely support an endoscopic instrument when the surgeon is not handling the instrument" (Col. 5, lines 23–26, of Brinkerhoff) Not only must the first toroidal section of the Brinkerhoff device be tall enough to support an instrument, it must inherently be stiff enough to do so, while also maintaining a seal. It is clear that in order to maintain a seal, a hand passing through the center of the device must be significantly restricted. The pressure and surface area of the device on the hand must limit forward and rotational movement within and below an incision. In addition, the overall height of the device, including those portions above, within, and below, the incision produces a fulcrum of significant overall length. It would be difficult, if not impossible, for a surgeon to reach all regions within the peritoneal cavity with the hand or an instrument, particularly those areas lateral to the incision and just below the body wall. The specific design of this device ultimately limits its purpose: to permit access to, and operation within, the peritoneal cavity.

A secondary problem associated with the Brinkerhoff device relates to the need to keep it inflated in order to effect a seal. The application of pressure to keep the device operable renders this device subject to unexpected failure, whether by a defect or weakness in the material, or by a failure of the equipment used to maintain the pressure. If the need to keep a seal of the incision is important, such concerns render the Brinkerhoff device less than suitable.

Another problem related to limited access occurs with procedures requiring specimen removal. While some specimens have been removed through the small access incisions, and others removed through innovative approaches—e.g., the vagina—many require a separate incision for removal. However, these incisions have generally been smaller than those of open procedures and have preserved most of the benefit of a laparoscopic approach.

Some surgeons have adopted modified laparoscopic approaches when specimen removal is an issue. Internal observations and some manipulations are performed with insufflation via laparoscope. Some manipulations and specimen retrieval are performed without insufflation through a small 4–6 cm incision. Some surgeons have placed their hands into the wound under laparoscopic visualization and with insufflation. The seal is maintained by securing the abdominal wall to the hand with surgical ties attached to the abdominal wall. These approaches still contain many negative aspects. The pure laparoscopic portion is performed with diminished perception, as outlined above. The pure open portion is performed at the level of the skin with almost no access to the body cavity. In addition, combined approaches can be difficult. Committing one hand to the abdominal cavity limits a surgeon's usefulness for other tasks. The option of withdrawing the hand is therefore desirable. However, conversion from one approach to the other is difficult because the larger incision must be resealed on each occasion to re-establish pneumoperitoneum. This added time limits its frequent use, though this is increasingly desirable with increasing operative complexity.

Finally, there has been concern about wound contamination during laparoscopic surgery particularly the implantation of tumor cells. The etiology of this problem is unclear. It may be a systematic problem with a particular element of the technique such as insufflation where positive pressure venting through the incision results in contamination. Another systematic problem might be direct contamination during specimen removal. The anecdotal occurrence of these problems suggests a more isolated and less systematic error, such as poor tissue handling technique. However, these concerns and the lack of understanding have limited the application of the technique.

What is needed is a surgical technique that combines the observational advantages of an endoscope and the tactile sensation of traditional open surgery. What is also needed is a surgical technique that minimizes the size and number of incisions required to perform operations, particularly abdominal operations, yet preserves the surgeon's ability to change with the changing requirements of complex operations. Still further, what is needed is a surgical device that permits the simultaneous use of endoscopic observation in combination with the advantage of physical contact with that portion of the body operated upon. What is yet further needed is a device that facilitates procedures using both endoscopic and tactile approaches, allows quick conversion between approaches, and therefore increases the surgeon's flexibility to choose the best approach. What is also needed is a device that can be used in video-assisted surgery, which can effectively maintain insufflation of the body cavity when that technique is used, and that can be used to minimize or prevent wound contamination. Finally, what is needed is a trocar-based system to enable the introduction of a variety of devices for tactile manipulation within the body cavity while minimizing the size of the incision or incisions required for such activity.

SUMMARY OF THE INVENTION

It is an object of the present invention to introduce a surgical technique that minimizes patient trauma yet avoids the expensive and time-consuming limitations inherent with currently existing laparoscopic techniques. The technique incorporates the use of an endoscope for visual observation in combination with the tactile manipulation associated with traditional open surgical techniques. The technique preserves the surgeon's adaptability to a changing environment. It is also an object of the present invention to provide a surgical device that provides for a reduction in the size and number of incisions required to perform surgery. It is another object of the present invention to provide a device suitable for accessing the body cavity using surgical instruments and/or a surgeon's hand or fingers. The device is designed to maintain pneumoperitoneum of an expanded abdominal cavity. It is yet another object of the present invention to provide the capability for tactile manipulation while also protecting the wound from contamination that may be present during the surgical procedure. Finally, it is an object of the present invention to provide a trocar-based system to enable the introduction of a variety of devices for tactile manipulation within the body cavity while minimizing the size of the incision or incisions required for such activity.

These and other objectives and advantages are achieved in the present invention by the introduction of a novel access device through which a tube, an instrument, or a surgeon's hand or fingers may be inserted. The access device is further designed to prevent contamination of the incision into which it is inserted by isolating the wound from the body cavity.

The use of the access device results in a novel surgical method that permits easy access by an instrument or a human hand into a body cavity for the purpose of performing surgical operations including video-assisted surgery.

The access device of the present invention has a sealing component that can be designed to fit any size incision, that permits access to the body cavity by surgical instruments and/or a surgeon's hand, and that ensures a complete seal of the incision so that insufflation can be maintained when insufflation is used. In general, the access device is a sealing ring that is either adjustable so that it fits into the incision, regardless of the size of that incision, or that comes in a plurality of fixed sizes to be selected as required for a particular incision. The sealing ring of the present invention is fabricated of a material and of a thickness sufficient to allow the user to manipulate it into place in the incision. It is expected that a viscoelastic material such as latex is suitable, though metal variations are possible. The ring preferably seals the interior as well as the exterior portions of the incision. In that regard it fits into the incision, extends a distance along the patient's skin, and extends a distance along the interior wall of the body cavity around the incision. By this design the sealing ring remains in place regardless of the insertion or removal of equipment or the surgeon's hand. Moreover, the ring provides a seal at two locations, the exterior and the interior of the body wall. In this way, when pneumoperitoneum is desired, it is certain that expansion will be maintained. The sealing ring also provides protection of the wound from contamination by intra-abdominal contents. The sealing ring may provide sealing at one, or alternatively at other locations, dependent upon the particular surgical procedure.

The sealing ring of the present invention is advantageous in that it provides a simpler means for accessing the body cavity than is currently available. It provides a flexible access port rather than the rigid, laterally limited tubes currently in use. In addition, the access device of the present invention does not require inserting equipment through a long tube. Instead, the incision is effectively sealed with a low profile device extending slightly above the patient's skin. Moreover, it is not obligatory to use dangerous entrance trocars. The sealing ring may include a sealing cap that can be used by the surgeon to further ensure protection of a sealed wound when the incision is not being used, particularly when pneumoperitoneum is to be maintained.

In a particular embodiment of the invention, the sealing ring preferably is a fixed, non-inflatable device that is sufficiently compliant that it may be moved about without causing a significant loss of contact with the incision. As the device does not have to be pressurized, the possibility of undesirable failure and, therefore, loss of a seal, does not exist. In addition, the sealing ring preferably extends no more than 50 millimeters above the exterior surface of the skin surrounding the incision. This may be achieved by making that section of the ring no more than two inches thick. Similarly, the portion of the sealing ring that is in contact with the body wall opened by the incision must be thin enough to maximize maneuverability within the peritoneal cavity. It must also be pliable or compliant, rather than stiff or rigid, so as to enable lateral movement within and below the incision. Finally, the portion of the sealing ring running along the interior body wall should be relatively no thicker than the outer section and should preferably be much thinner—on the order of 0.1 millimeter to 10 millimeters. As a result of this arrangement, the present invention creates minimal contact between the sealing component and that which is inserted into the cavity formed. In that way, interference with lateral movement is minimized.

A supplemental yet distinct device that may be used to perform the surgical techniques of the present invention is a modified surgical glove. The modified surgical glove is a component of the present invention when the surgeon wishes to place his or her hand or fingers into the body cavity. It is also distinct in that it is designed for application in a laparoscopic procedure where pneumoperitoneum must be maintained. The modified glove includes an extended rear portion that is designed to cover the surgeon's arm up at least to the wrist and beyond that point if necessary. The application of such a glove simultaneously with the sealing ring permits the surgeon to be in direct physical contact with the contents of the body cavity without detriment to pneumoperitoneum. As a result, the visual advantages of endoscopy can be used in conjunction with the advantages of direct tactile manipulation. In this way, incision sizes and numbers may well be minimized.

An optional feature of the modified glove of the present invention is the inclusion of equipment access regions that form portions of the fingers of the glove. These access regions are designed to provide introduction of items such as cautery electrodes, suction, irrigation, and the like. Through this novel glove design the surgeon literally has at his or her fingertips essential equipment that can be used simultaneously with the surgeon's physical contact with the region that is being manipulated. In addition to reducing the time involved in the surgical procedure, this glove modification also reduces the number of incisions required to perform the procedure. As previously noted, the surgical techniques presently employing endoscopy rely upon the use of multiple relatively small incisions for the introduction of various pieces of supplemental equipment. The present surgical glove may reduce that need and, likely, the trauma and morbidity for the patient.

The sealing ring as well as the modified glove of the present invention both lead to new surgical techniques that are anticipated to reduce operating time and patient trauma. As a result, patient care costs may be reduced. The novel surgical technique of the present invention includes the use of an endoscope to view the body region(s) to be worked on without making large incisions. However, the technique has broader application in that the sealing ring of the invention provides a surgeon with more technical options than currently available. A single access incision may be made and used for conducting all steps of the procedure. That is, the incision may be made just long enough to allow insertion of a tube for a scope, to allow access for larger instruments, for introduction of the surgeon's hand(s) or finger(s), and for specimen removal. Endoscopic observation and manipulations may be made, minimizing incisional trauma. Tactile manipulations may be made, giving the surgeon better control over tissue and decreasing operative time. Both methods may be used simultaneously, or in a sequence of the surgeon's choice not limited by excess time converting from one approach to the other. This operating system offers the advantages of open and laparoscopic surgery to be realized with few of the disadvantages. It allows the surgeon the flexibility to easily adjust the procedure as indicated by the dictates of each individual case. If the surgeon requires an additional access port or ports, additional minimal incisions may be made. There is no limitation on the particular size of the incision(s), apart from achieving the goal of minimizing patient trauma. It is to be understood that each incision can be fitted with a sealing ring; however, it is not obligatory and so the device may be used in conjunction with standard equipment inserted as with a trocar. After insertion of the sealing ring of the present invention where desired, standard equipment may be installed and removed, and organs may be withdrawn as necessary. The endoscope may also be placed through any incision. The isolation of the wound by the sealing ring minimizes contamination. The combination of the use of an endoscope and the sealing ring of the present invention permits the surgeon to access the body cavity directly but with minimal intrusion. It is anticipated that the video-assisted tactile procedures enabled by the present invention will be less dependent upon repetitive training of a specific team of individuals in order to carry out particular surgery quickly and successfully. The learning curve would therefore be reduced and acceptance of the technique more likely.

A modified trocar system of the present invention may alternatively be used alone or in conjunction with the sealing device previously described. The modified trocar system includes a trocar device that is insertable down through an existing relatively larger incision and then directed through the body cavity and directed outwardly at a remote location to create a second, smaller incision. That is, the trocar device is directed in a much safer inward-to-outward manner, rather than the standard outward-to-inward direction that may result in accidental damage to the viscera within the body cavity as the effort to pierce the skin is made. The resulting second relatively smaller incision may then be used to deploy equipment of interest, while the surgeon may manipulate such equipment from the first, larger incision. Alternatively, larger equipment may be deployed through the first incision and linked to equipment inserted through the second incision. In this way, the number and size of the incisions required to insert equipment and materials of interest into the body cavity may be minimized without compromising the type of equipment deployed or the surgeon's ability to retain tactile contact with organs to be manipulated.

Specific options to the design of the modified trocar system of the present invention include a rigid or compliant flange that may be inserted through the larger incision to be placed in contact with the underside of the body wall adjacent to the incision. The modified trocar with flange may be inserted directed through the incision or through the sealing ring of the present invention as previously described. The flange may be placed in direct or indirect contact with that underside or interior surface of the body wall. As with conventional trocars, the flanged trocar of the present invention includes a very sharp incision-making end for puncturing the skin and establishing a very small incision. At the opposite end of the modified trocar a lifting mechanism, such as a unitary knob that is the top of the flanged trocar, may be employed to draw the body wall in the area of the sealing ring upward to form a tent for the surgeon to easily place his or her hands therein. Alternatively, that end of the flanged trocar may include a retention mechanism, such as a threaded socket, into which a removable handle may be inserted. This handle may be used to pull the trocar upward as desired when deployed in the incision. Use of the flanged trocar enables the surgeon to selectively provide more maneuvering room within the body cavity without establishing and maintaining conventional insufflation.

More generally, the modified trocar system of the present invention may be a two-part system wherein a first component is deployed through the smaller second incision, and a second component is deployed through the larger first incision. The second incision is preferably created by as a "reverse" incision established by inward to-outward pressing of the sharp end of the trocar at a location distant from the first incision but initiated through the first incision. A coupling device, such as a tube, bar, or the like with a linking component at one end and a manipulating mechanism at the other end is designed to be inserted through the second incision, with the linking component designed to be placed in the body cavity. One or more attachable operating devices, such as a cautery device, an irrigation tube, a retractor, etc., may then be passed through the larger first incision and connected to the linking component of the coupling device. The operating device may be expandable within the body cavity. However, conventional operating devices may be deployed through the larger incision if desired, and then linked to the coupling device for manipulation through the smaller incision. It is to be noted that a multi-device piece may be detachably affixed to the coupling device and various devices associated therewith selectably activated all within the body cavity, thereby minimizing the movement of devices in and out of the incisions.

The advantages of the modified trocar system are: 1) the relatively greater safety of "inside-out" trocar movement; 2) the ability to deploy and use within the body cavity operating devices that are otherwise relatively larger than the size of the smaller incision; and 3) the ability to deploy and use a plurality of operating devices within the body cavity without the need to move one in and out of the cavity in order to make room for insertion of the next one, and so on.

These and other aspects and advantages of the present invention will be better understood with reference to the following description, the drawings, and the appended claims.

DESCRIPTION OF THE PREFERRED EMBODIMENTS OF THE INVENTION

Figure 1:
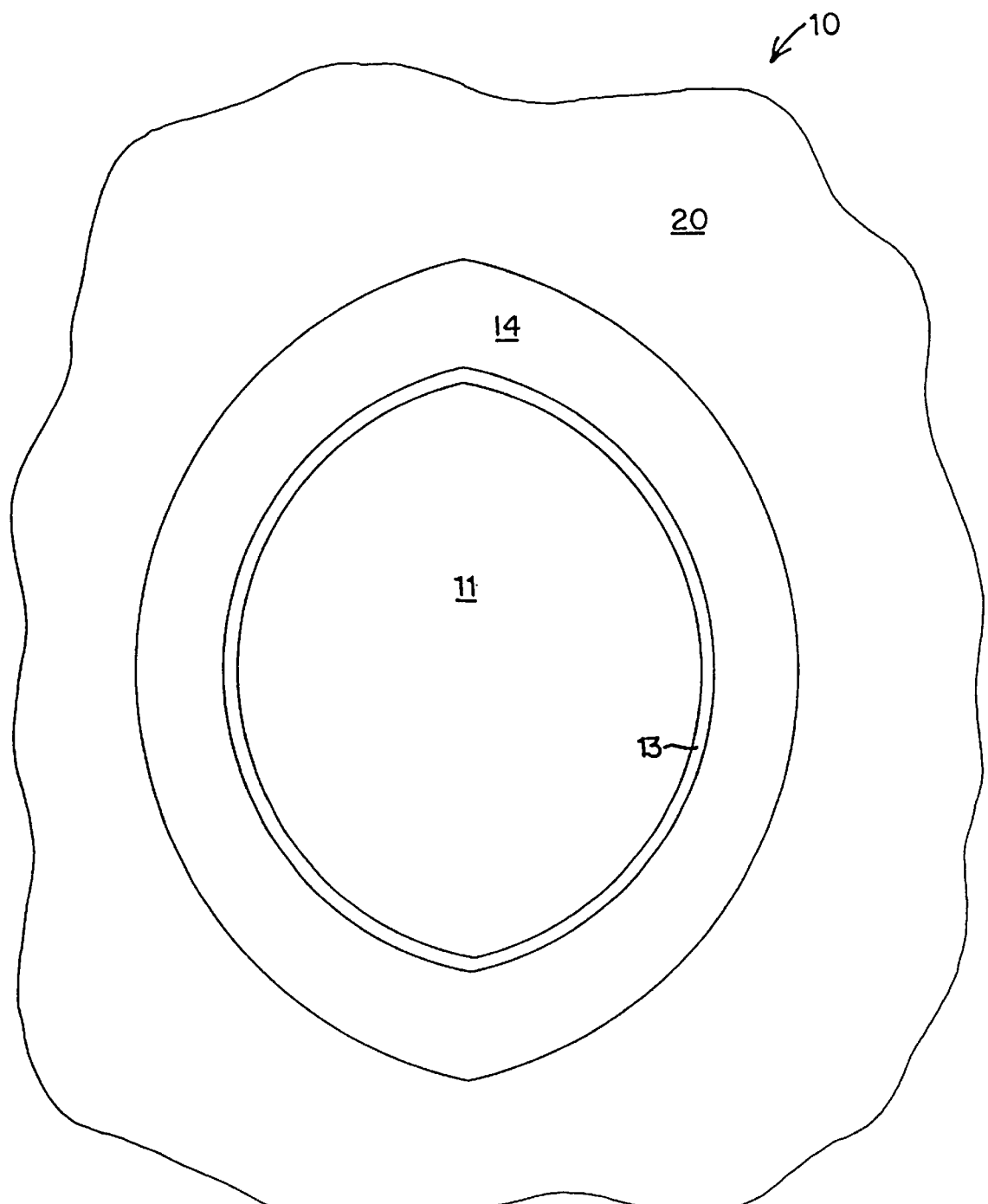
FIG. 1 is a top view showing the sealing ring of the present invention.
Figure 2:
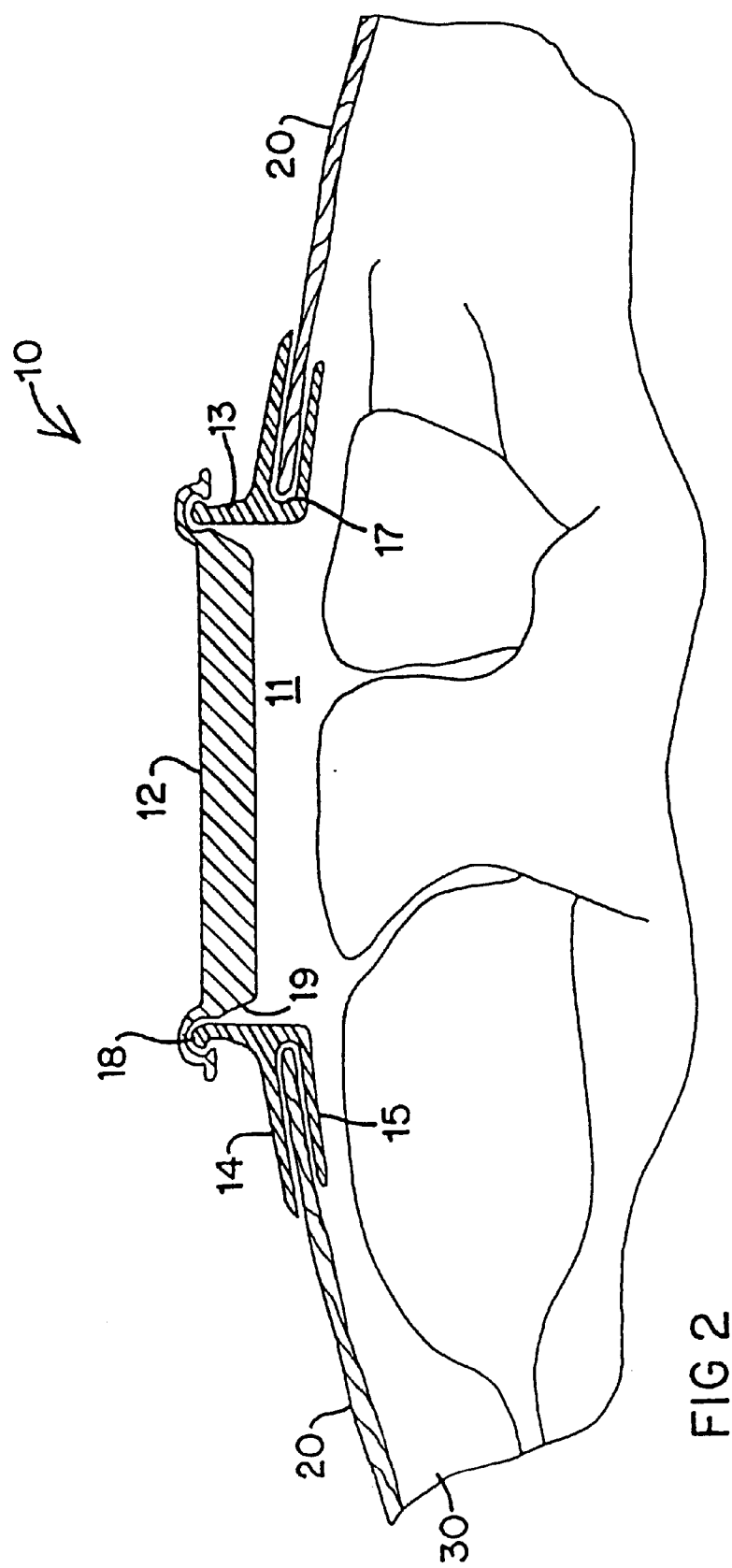
FIG. 2 is a simplified cross-sectional view of the sealing ring of the present invention in place in an incision of a body wall and also showing a temporary sealing cap.
Figure 3:
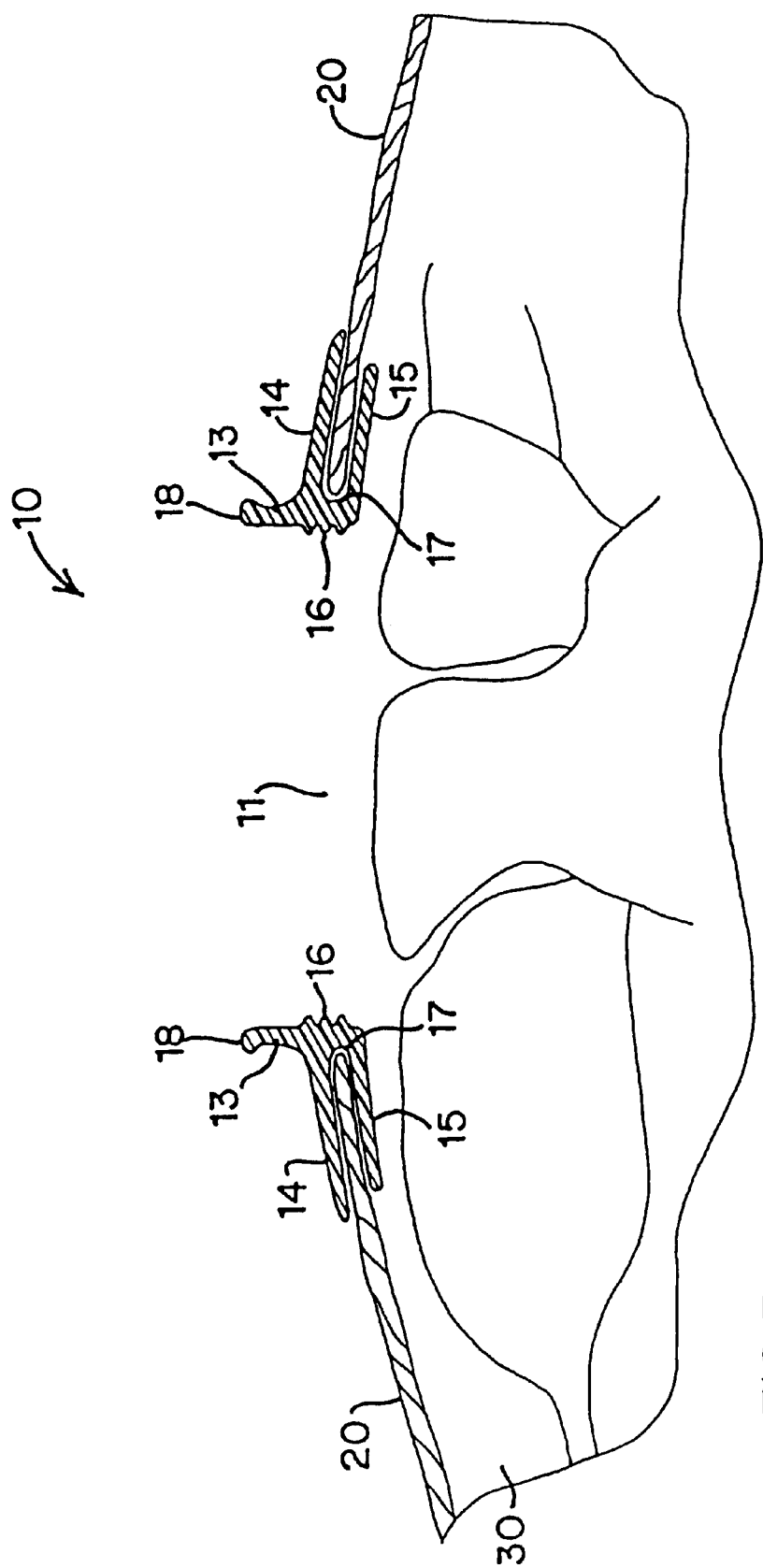
FIG. 3 is a simplified cross-sectional view of the sealing ring of the present invention in place in an incision of a body wall without the sealing cap.
Figure 4:
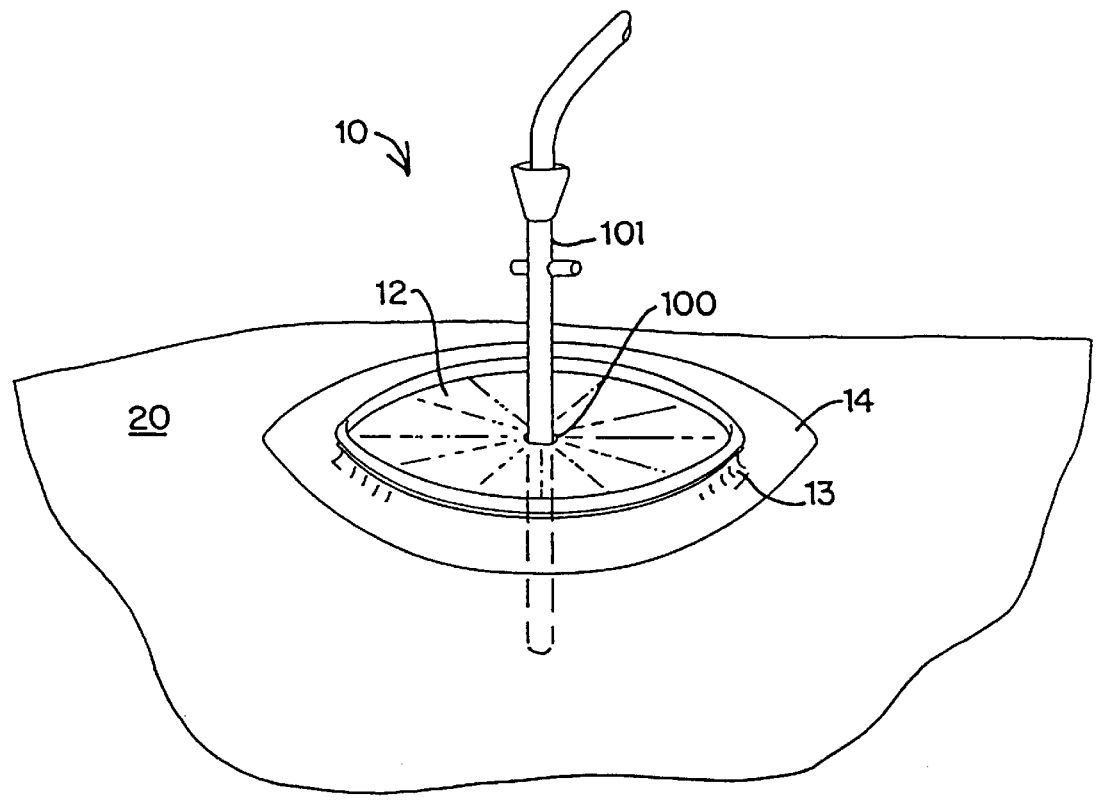
FIG. 4 is a perspective view of the sealing ring of the present invention in an incision and also showing the sealing cap with an optional cap hole through which a tube is inserted.
Figure 5:
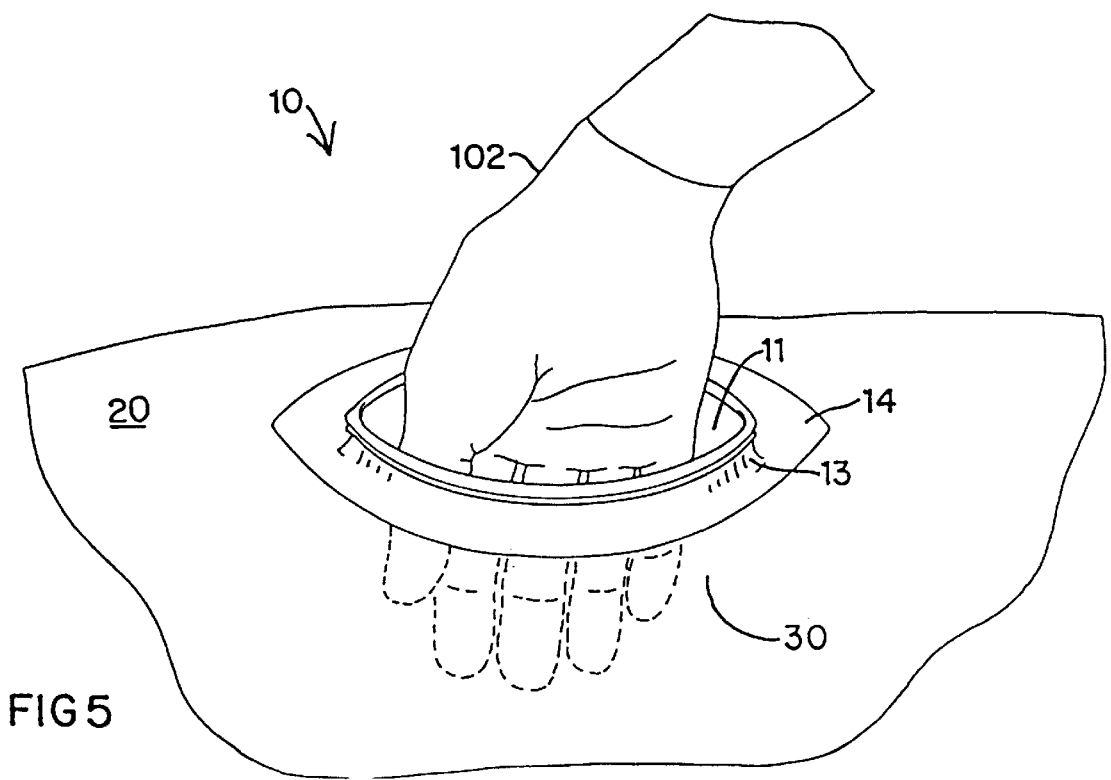
FIG. 5 is a perspective view of the sealing ring of the present invention in place in an incision of the body wall and also showing a surgeon's hand positioned therein.
Figure 7:
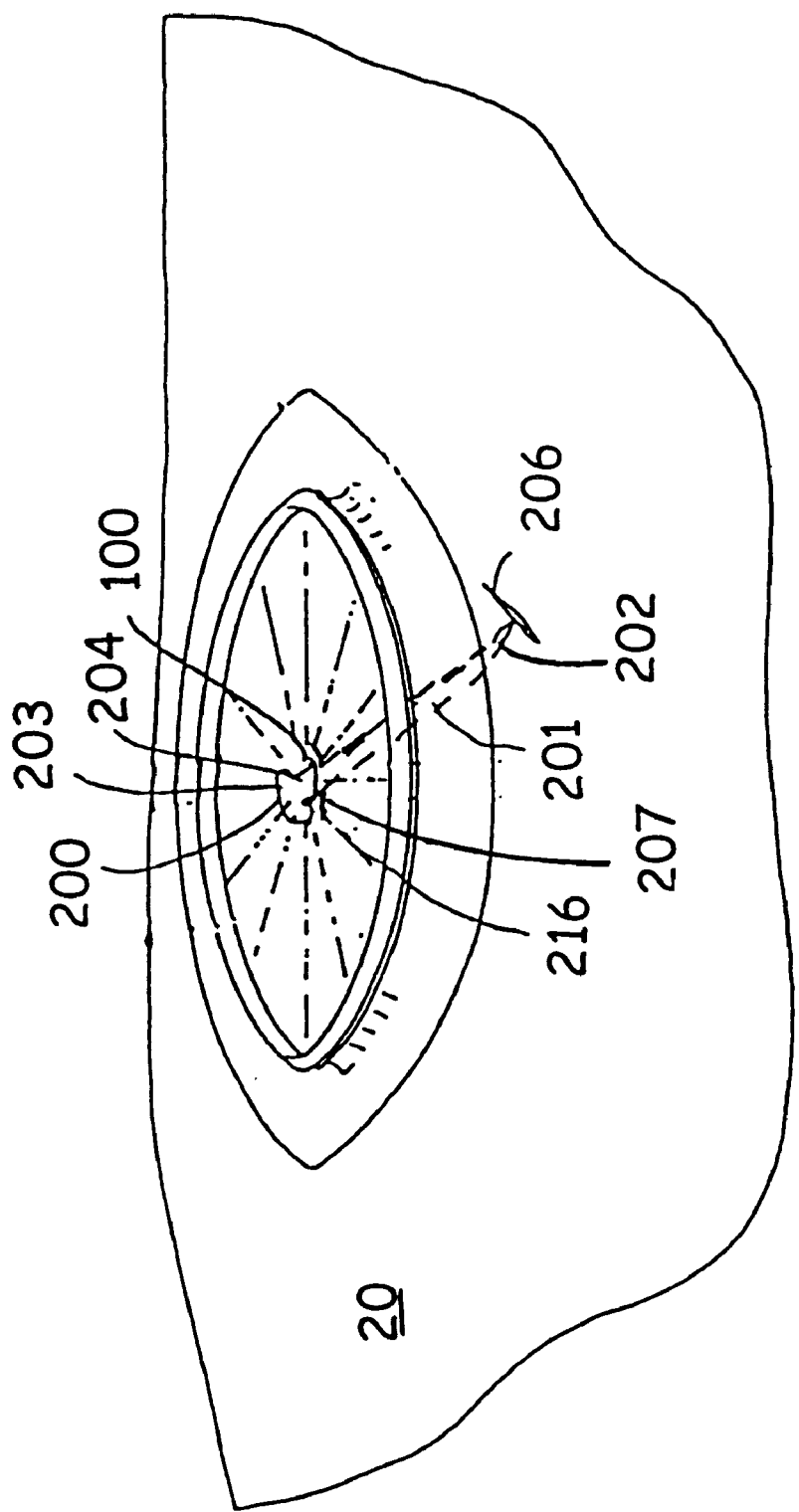
FIG. 7 is a perspective view of the modified trocar system of the present invention in the process of being deployed through a sealing ring of the present invention.
Figure 8:
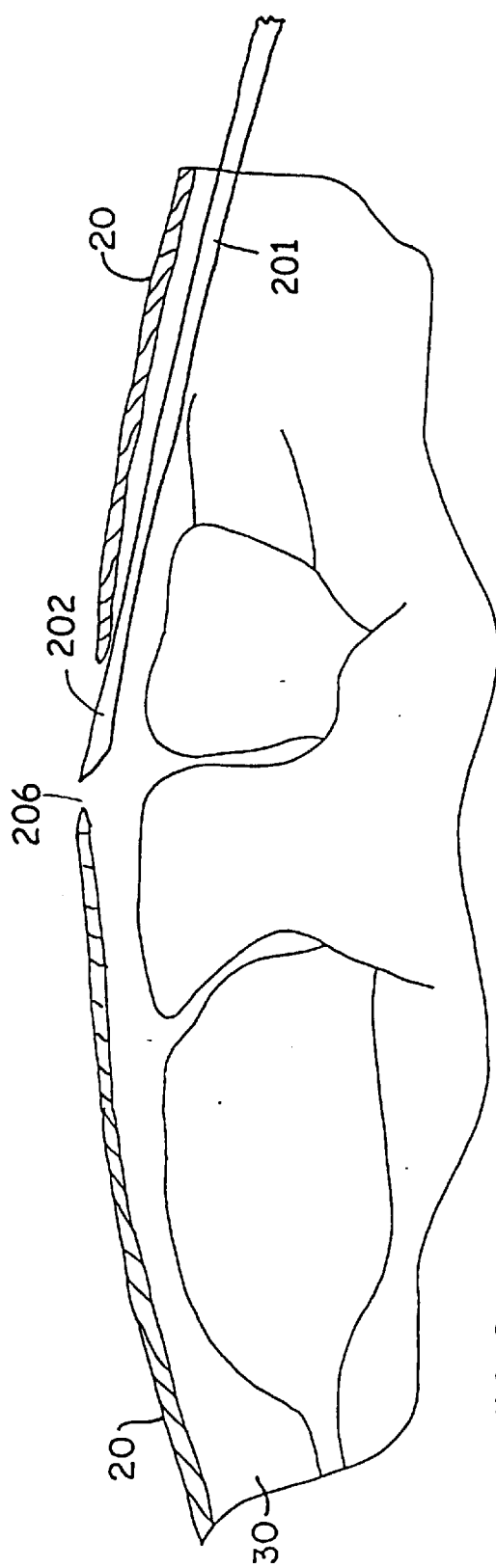
FIG. 8 is a side view of the smaller second incision established by inside-out operation of the modified trocar system of the present invention.

The present invention includes a multi-function port device that permits a surgeon the flexibility to perform tactile surgery, endoscopic surgery, or video-assisted surgery, all through the same incision, if desired. The use of the device leads to novel surgical techniques. The multifunction port device is a sealing ring 10, illustrated in FIG. 1, that acts to isolate a body wall 20 from surgical procedures carried out within a body cavity 30, as illustrated in FIGS. 2–3. The sealing ring 10 is designed to permit easy access of an instrument tube 101, as shown in FIG. 4, or a surgeon's hand or fingers 102, as shown in FIG. 5, into the body cavity 30. An optional component of the present invention is a surgical glove 40, shown in FIG. 6, that may be used so that a surgeon can have direct physical contact with the contents of the body cavity 30. In addition, the surgical glove 40 may include one or more accessory regions 41 for delivering surgical instruments to the surgeon's fingertips within the body cavity 30. The accessory regions 41 may be integral parts of the surgical glove 40 or they may be detachably connected thereto. An alternative modified trocar system 200 of the present invention is shown with respect to FIGS. 7–9.

The surgical technique of the present invention involves the creation of a first incision of a size determined by the surgeon for the particular procedure to be carried out. This first incision may be the only one required and it may be used to deploy equipment and/or the surgeon's hand or fingers within the body cavity 30. Additional incisions of varying sizes may be created at the outset or during the course of the procedure as required. The incision or incisions will typically range from about five millimeters to about 15 centimeters in length. The sealing ring 10 having an inner opening region 11 is preferably placed into each incision. However, it is to be understood that it is not necessary to place the sealing ring 10 in every incision, particularly if an incision is to be used for only one purpose. If it is necessary to expand the body cavity 30 through insufflation means, or if it is desired to prevent any contamination from entering or exiting the inner opening region 11, a sealing cap 12 may be affixed to the sealing ring 10 to close the inner opening region 11. The sealing cap 12 may be removed as required from the sealing ring 10 of a particular incision in order to access the body cavity 30 through the inner opening region 11.

As indicated, the sealing ring 10 provides an access port for easily inserting equipment into the body cavity 30 and for easily removing portions of the contents of the body cavity 30, among other advantages. The sealing ring 10 is preferably fabricated of a non-metallic material such as polyethylene or latex that is approved for use in surgical procedures. The sealing ring 10 is preferably sufficiently flexible so that it can be fitted into an incision and returned to its original shape upon deployment in the incision. It is contemplated that the sealing ring 10 will be fabricated in a variety of sizes, generally having inner dimensions ranging from about five millimeters to about 15 centimeters. A ring wall 13 will have a thickness of about 0.1 to about 1.0 millimeter.

In order to minimize contamination of the body wall 20 such as by extraction of a tumorous organ therethrough, and/or in order to provide an effective seal to maintain expansion of the body wall 20 when the body cavity 30 is insufflated, the sealing ring 10 includes a first extended region 14 and a second extended region 15. The first extended region 14 and the second extended region 15 are integrally connected to the ring wall 13 and extend outwardly therefrom, and can range in length from about 5 centimeters to about 20 centimeters. The preferred embodiment of ring wall and extended regions is fabricated as a unitary piece composed of non-metallic materials such as polyethylene or latex, approved for surgical procedures. Alternative embodiments include the use of metals or fabrication in separate sections bonded or otherwise joined together.

The combination of the first extended region 14 and the second extended region 15 of the sealing ring 10 increases isolation of the body wall 20 from contaminants and secures a vapor seal when necessary, subject to sealing of the inner opening region 11. The second extended region 15 located under the body wall 20 within the body cavity 30 may also be used as a simple but effective means to lift the body wall 20 to expand the space available within the body cavity 30 that is accessible by the surgeon. In an alternative embodiment of the sealing ring 10 for this purpose, the ring wall 13 includes inner ring threading 16 that can be used for attachment of a threaded trocar or simply a threaded rod. After locking the trocar or rod to the inner ring threading 16, the surgeon or an assistant may simply pull up on the trocar or rod, thereby pulling up the integral second extended region 15 which in turn pulls the body wall 20 up to form a tent. While this technique provides a limited expansion of the area accessible within the body cavity 30, it is a less expensive procedure than insufflation, provided the second extended region 15 is sufficiently rigid or includes means to keep it in position.

An alternative device for operating on a patient is a modified trocar system 200 that may be used in an inverted or "inside-out" position. Specifically, as shown with regard to FIGS. 7–8, a small incision 206 may be made remote from the region to be worked on by the surgeon and the trocar 200 placed through a relatively larger incision 210. Specifically, the body wall 20 is punctured from the inside out by the trocar 200 at the site to be worked on so as to establish smaller incision 206. Of course, the incision 210 may be protected by the cap port 100, described herein, of the sealing cap 12 associated with the sealing ring 10 previously described. The incision 206 is preferably smaller than incision 210 so that subsequent patient discomfort and recovery time may be minimized. It is particularly useful for enabling the surgeon to conduct surgical activities therein in combination with activities undertaken through the incision 210. The trocar 200 includes a trocar body 201, a first end 202 having a sharp incision-creating terminus, and a second end 203.

Figure 9:
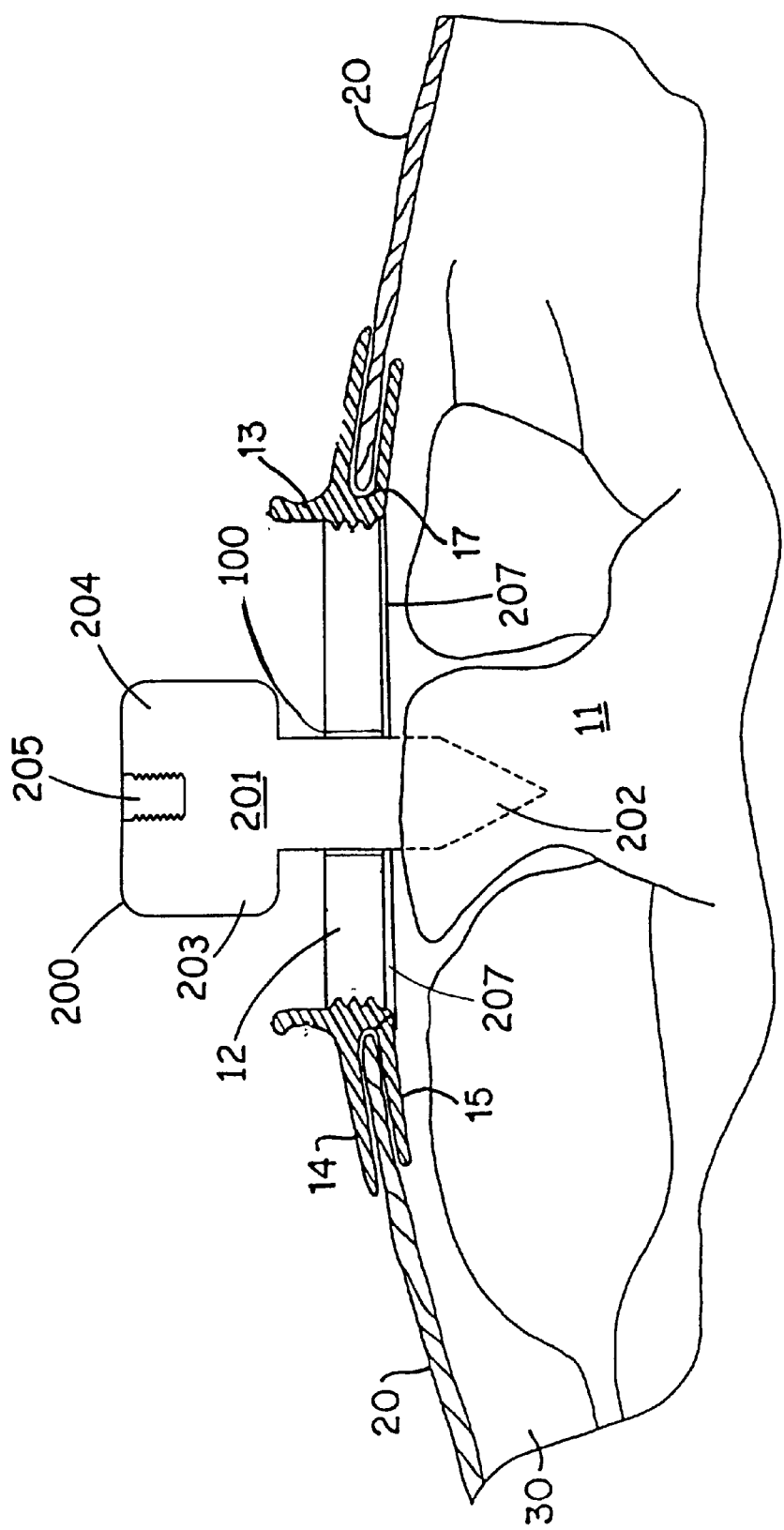
FIG. 9 is a side view of the modified trocar system of the present invention using the optional flange arrangement.

As illustrated in FIG. 9, the trocar 200 may include an extended flange 207 that is either formed as a unitary part of the trocar body 201, or that may be coupled thereto. It may then be pulled partially back until the flange 207 contacts the interior surface of the body wall 20 or the inside surface of the ring 10 or cap 12. Its profile is such that it preferably extends slightly above the patient's skin when it is in place. That portion of the modified trocar 200 at the patient's skin may include a lifting mechanism 204, such as a knob 204 fitted or otherwise connected to the modified trocar 200 such that the trocar 200 can easily be lifted, thereby forming a tent of the body wall 20 in the vicinity of the incision 206. Alternatively, a threaded socket 205 may be used to permit the surgeon to deploy some other form of removable lifting element therein. The trocar 200 can be placed in the periphery of the cavity 30 or wherever exposure is required. The surgeon can expand the area of interest—not merely the area of the incision into which the sealing ring 10 has been inserted—by pulling upwardly on the lifting mechanism 204 so that the flange 207 pulls the body wall 20 upwardly. This modification avoids the cost, complexity, and hazards of insufflation. It also decreases the risk of visceral injury associated with standard trocar placement. The sealing ring 10 in conjunction with some other type of lifting mechanism can similarly be used in this way so as to take advantage of using negative pressure.

Figure 10:
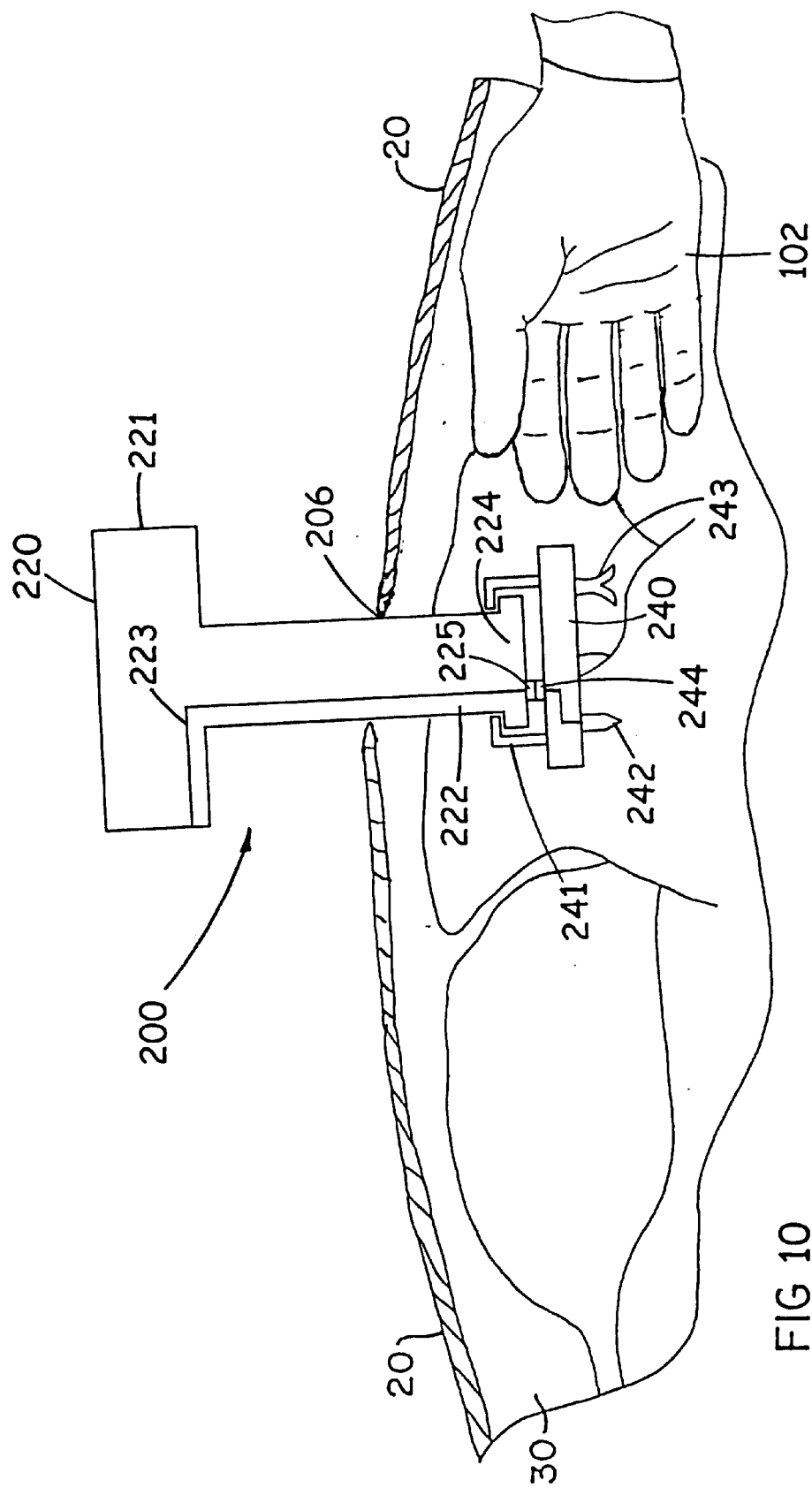
FIG. 10 is a side view of the modified trocar system of the present invention as an alternative two-part system including a manipulation structure and a coupling structure.

As illustrated in FIG. 10, the modified trocar system 200 of the present invention may alternatively include a first manipulation structure 220 and a second deployment structure 240. The manipulation structure 220 may include a manipulation end 221 that enables a surgeon to move the structure 220 into and out of the incision 206, or otherwise to manipulate a lower structure end 222 within the body cavity 30. The structure 220 is preferably of cross-sectional dimensions to enable its deployment within the smaller incision 206. The end 221 may be of any shape and size, preferably ergonomic in nature. It may also be used to deploy components of interest thereon or therein, such as digital readouts, insertion mechanisms for tubes, wires 223, and the like, as required by the particular procedure to be performed within the body cavity. The lower end includes a coupling component 224 for detachably linking the structure 220 to the structure 240.

The structure 240 includes a coupling component 241 for linking the structure 240 to the coupling component 224 of the manipulation structure 220. The component 241 may be detachably affixable to the component 224. Alternatively, it may be a rotatable device capable of rotating about the lower end 222 in order to present to the surgeon any one of a plurality of operating devices, such as a cautery device 242 or a retractor 243, for example. It is to be noted that the structure 240 is designed to be deployed through the:larger first incision 210, and may be manipulated by the surgeon's hand 102 within the body cavity 30 to contact the structure 220 for coupling thereto. Means for interfacing the particular operating device or devices with the structure 220 may be included as part of the trocar system 200. For example, rotatable contacts 225 and 244 may be employed to establish electrical contact with the cautery 242. It can be seen that the use of the two detachably connectable structures 220 and 240 enable the surgeon to deploy and manipulate relatively larger equipment using relatively smaller incisions. Further, such manipulation may occur within the body cavity without the need to continuously move such equipment in and out of the incisions.

When the body cavity 30 is in a state of pneumoperitoneum, maintaining an effective seal at the incision, including between the body wall 20 and an outer ring wall 17 of the sealing ring 10, is of particular importance. Given the skin's general pliability, there is already an effective seal between the body wall 20 and the outer ring wall 17. However, it is important to ensure that little vapor escapes via the inner-opening region 11. When a particular incision is not in use, this sealing may be achieved in the present invention through the application of the sealing cap 12, which is preferably fabricated of a material compatible with that of the sealing ring 10. The sealing cap 12 may be much like a sealing lid typically used to maintain the seal of a colostomy appliance. A cap securing ring 18 may be used to secure the sealing cap 12 to the sealing ring 10, or an inner cap wall 19 of the sealing cap 12 may be threaded so as to be compatible with threading of the outer ring wall 17. The sealing cap 12 may further be designed with a cap port 100 so as to provide access to the body cavity 30 through the sealing ring 10. The cap port 100 may be of any inside dimension suitable for insertion of instruments such as needles, aspiration tubes, etc. When the body cavity 30 has been expanded by insufflation, the cap port 100 must also include sealing means, such as a viscous gel, or a rubberband-like device, in order to prevent vapor escape either through the cap port 100 or from between the cap port 100 and the instrument inserted therein.

Continuing with the discussion of the novel surgical technique of the present invention, particularly with regard to video-assisted surgery, an endoscope tube with endoscope therein, is inserted into the incision, or one of the incisions if a plurality have been made. The incision into which it is inserted may not initially, or ever, be sealed by the sealing ring 10. The surgeon can direct the movement of the endoscope and view the interior of the body cavity 30 either directly or via a video monitor. An incision may be used to deploy a trocar with a cannula for insufflation of the body cavity 30 if necessary. Other incisions may be used to deploy instruments including, but not limited to, aspiration means, cautery electrodes, suction means, and other instruments commonly used by surgeons. These additional openings eliminate the restrictions associated with prior use of a tube to deploy such instruments. Alternatively, a single incision may be used, as noted, to insert and remove various instruments, and or the surgeon's hands or fingers. An incision having the sealing ring 10 may be used to deploy an instrument, which may be left there while a procedure is carried out elsewhere, without concern that the idle incision will be contaminated. This further increases the surgeon's flexibility during the surgical procedure.

The first and any other incision created may be used by the surgeon to access the body cavity 30 directly by hand so that the surgeon has physical contact with the contents of the body cavity 30 that are the subject of the surgical procedure. The shorter profile of the sealing ring 10 as compared to standard equipment tubes permits this option. In this way, the surgeon can view the body cavity 30 via a scope, if desired, and manipulate the contents therein by hand through that or another incision. As a result, the incision required to insert the surgeon's hand or fingers—or to move some or all of an organ out of the body cavity 30—need only be large enough to fit the hand, the fingers, or the organ, as shown in FIGS. 4 and 5. The incision does not have to be extended in order to permit the surgeon to view the extended area of interest. Through the use of one or at least a minimal number of minimally sized incisions, essentially all surgical procedures may be performed with reduced trauma to the patient. In addition, by initially creating all of the required incisions at the outset of the procedure, the operation can proceed more quickly than under prior endoscopic procedures where unexpected problems require the creation of unanticipated larger incisions.

Figure 6:
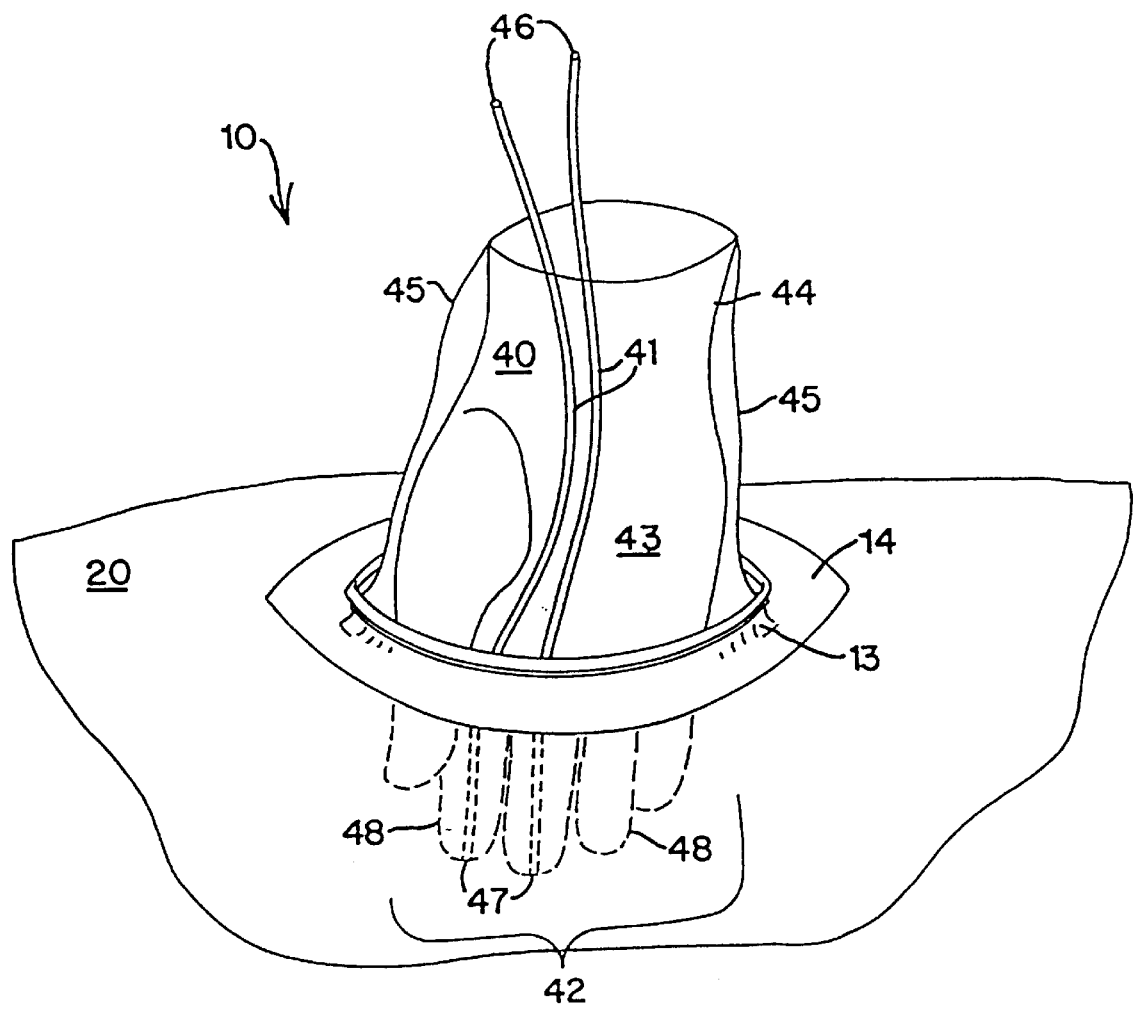
FIG. 6 is a perspective view of the present invention including the modified surgical glove.

An additional device that may be used in conjunction with the technique of the present invention is the surgical glove 40 shown in FIG. 6. The surgical glove 40 includes a finger region 42, a palm region 43, and an optional extended arm region 44. The introduction of the extended arm region 44 permits the surgeon to move his or her arm well into the body cavity 30 when desired. The surgical glove 40 may be fabricated of any material generally used in surgical procedures, including, but not limited to, latex. When the surgeon wishes to insert his or her hand through the sealing ring 10 and into the body cavity 30, the surgical glove 40 of the present invention is designed so that a seal may be maintained, if required, during the procedure. This is preferably achieved by including glove sealing means, such as a glove tent 45, that may also be fabricated of latex, that may be secured to the first extended flange 14 of the sealing ring 10, and that permits movement of the surgical glove 40 in and out of the incision.

A key feature of the surgical glove 40 is the inclusion of one or more accessories that may be affixed to, or that may be an integral part of the surgical glove 40. The accessory regions 41 are generally designed to extend from the extended arm region 44 down to the end of the finger region 42 and may simply be hollow tubes fabricated of a non-metallic material such as polyethylene. Alternatively, they may be located at the end of the finger region 42 for introduction of solid devices, such as cautery units, or any other device that does not require a hollow tube. When provided as individual detachably connected tubes, for example, the accessory regions 41 may include VELCRO-brand sections that may be attached to corresponding VELCRO-brand sections on the arm region 44 and the finger region 42. When the accessory regions 41 are provided as detachable pieces, the surgeon may quickly remove a particular accessory, if necessary, such as, for example, when an aspirator becomes clogged and must be taken out. Alternatively, the accessory regions 41 may be integral components of the surgical glove 40 wherein they may be fabricated of the same material and at the same time as the surgical glove 40, or they may be of a different but compatible non-metallic material permanently attached to the surgical glove 40 such as by chemical bonding.

As previously indicated, the accessory regions 41 may be used to deploy surgical instruments to the body cavity 40. That is, a surgical instrument may be inserted into a first accessory opening 46 at the extended arm region 44, and moved to a second accessory opening 47 at a fingertip region 48 of the finger region 42. In this way, the surgeon has at his or her fingertips an instrument that can be immediately deployed to an area of interest. The use of instruments in this way further reduces the number of incisions that would otherwise be required during a procedure. It also enhances the surgeon's ability to integrate the advantages of tactile surgery with the usefulness of various instruments.

Although the present invention has been described with reference to particular preferred embodiment techniques and devices, variations on components and materials of fabrication, among other features, will be readily apparent to those skilled in the art. Therefore, it is to be understood that alterations and equivalents of the invention described may be made without deviating from its basic attributes.

I claim:

1. A surgical trocar system for use in performing surgical techniques, the trocar system comprising:
    a. a trocar insertable into a first incision of a body wall, said trocar having a first end and a second end, wherein said second end includes a sharp terminus capable of making a second incision in the body wall, and wherein said second incision is smaller than said first incision;
    b. a manipulation structure insertable into said second incision, wherein said manipulation structure has a manipulation end designed to be deployed external to the body cavity, and a coupling end designed to be insertable through said second incision into said body cavity; and
    c. a deployment structure designed to be detachably coupled to said coupling end of said manipulation structure, wherein said deployment structure is designed to be inserted through a first incision into the body cavity.

2. The trocar system as claimed in claim 1 wherein said deployment structure is rotatable.

3. The trocar system as claimed in claim 2 wherein said deployment structure includes a cautery device and a retractor device coupled thereto.

4. The trocar system as claimed in claim 1 wherein said deployment structure includes a cautery device detachably affixed thereto.

5. The trocar system as claimed in claim 1 further comprising at least one operating device mounted to said deployment structure.

6. A surgical instrument comprising:
    a manipulation structure having a manipulation end designed to be deployed external to a body cavity and a coupling end designed to be inserted into a body cavity; and
    a deployment structure detachably coupled to said coupling end of said manipulation structure, wherein said coupling end has smaller cross-sectional dimensions than said deployment structure so as to be able to be inserted into an incision that is smaller than said deployment structure, and wherein said deployment structure is designed to be introduced into a body cavity through a larger incision and detachably coupled to said coupling end of said manipulation structure within said body cavity.

7. The surgical instrument as claimed in claim 6 wherein said deployment structure is rotatable about said coupling end of said manipulation structure.

8. The surgical instrument as claimed in claim 6 further comprising at least one operating device mounted to said deployment structure.

9. The surgical instrument as claimed in claim 6 further comprising a plurality of operating devices mounted to said deployment structure.

10. The surgical instrument as claimed in claim 9 wherein said plurality of operating devices includes a cautery device and a retractor.

* * * * *